United States Patent
Kawakami et al.

(10) Patent No.: US 11,592,452 B2
(45) Date of Patent: Feb. 28, 2023

(54) DISEASE DETECTION METHOD

(71) Applicant: MCBI INC., Tsukuba (JP)

(72) Inventors: Daisuke Kawakami, Kyoto (JP);
Toshiya Matsubara, Kyoto (JP);
Kazuhiko Uchida, Tsukuba (JP); Kohji Meno, Tsukuba (JP)

(73) Assignee: MCBI INC., Tsukuba (JP)

( * ) Notice: Subject to any disclaimer, the term of this patent is extended or adjusted under 35 U.S.C. 154(b) by 344 days.

(21) Appl. No.: 16/630,686

(22) PCT Filed: Jul. 13, 2018

(86) PCT No.: PCT/JP2018/026582
§ 371 (c)(1),
(2) Date: Apr. 6, 2020

(87) PCT Pub. No.: WO2019/013341
PCT Pub. Date: Jan. 17, 2019

(65) Prior Publication Data
US 2021/0116464 A1    Apr. 22, 2021

(30) Foreign Application Priority Data
Jul. 14, 2017    (JP) ............................. JP2017-137724

(51) Int. Cl.
*G01N 33/68*    (2006.01)
*G01N 30/06*    (2006.01)
(Continued)

(52) U.S. Cl.
CPC ....... *G01N 33/6896* (2013.01); *G01N 27/623* (2021.01); *G01N 30/06* (2013.01);
(Continued)

(58) Field of Classification Search
CPC .... G01N 33/6896; G01N 27/62; G01N 30/06; G01N 30/72; G01N 30/88; G01N 33/60;
(Continued)

(56) References Cited

U.S. PATENT DOCUMENTS

2005/0048584 A1* 3/2005 Lamping .............. C07K 14/472
435/7.2
2008/0145885 A1* 6/2008 Bell .................... G01N 33/6851
436/15
(Continued)

FOREIGN PATENT DOCUMENTS

CA    2 467 073 A1    6/2003
DE    101 58 180 A1    9/2003
(Continued)

OTHER PUBLICATIONS

"Sample pretreatment for peptide in human blood plasma and blood serum", Biotage application note AN750, Biotage Japan Ltd., 2012, pp. 1-4, [online], [retrieval date Sep. 20, 2018] internet:<URL:http://www.biotage.co.jp/files/pages/news_66/file20120629_1.pdf>, non-official translation.
(Continued)

*Primary Examiner* — Jennifer Wecker
*Assistant Examiner* — Michael Paul Shimek
(74) *Attorney, Agent, or Firm* — Sughrue Mion, PLLC

(57) ABSTRACT

The present invention is a method for detecting a specific disease based on the result of a measurement in which the amount of a peptide serving as a biomarker contained in a biological sample is determined by using an LC-MS. A pretreatment process performed before the measurement using the LC-MS includes the steps of preparing a mixed sample solution by adding a stable isotope reagent and a trifluoroacetic acid to the biological sample, where the stable isotope reagent is prepared beforehand by labeling the
(Continued)

peptide with a stable isotope; boiling the mixed sample solution; injecting the mixed sample solution after boiled into a solid-phase extraction column to make the peptide be retained in the solid-phase extraction column; and passing a water-soluble organic solvent through the solid-phase extraction column to elute the peptide retained in the solid-phase extraction column and collect the eluate.

2 Claims, 5 Drawing Sheets

Specification includes a Sequence Listing.

(51) Int. Cl.
*G01N 30/72* (2006.01)
*G01N 30/88* (2006.01)
*G01N 33/60* (2006.01)
*G01N 27/623* (2021.01)

(52) U.S. Cl.
CPC .......... *G01N 30/72* (2013.01); *G01N 30/88* (2013.01); *G01N 33/60* (2013.01); *G01N 2030/067* (2013.01); *G01N 2030/8813* (2013.01); *G01N 2333/47* (2013.01); *G01N 2333/4716* (2013.01); *G01N 2333/974* (2013.01); *G01N 2800/2814* (2013.01)

(58) Field of Classification Search
CPC ..... G01N 2030/067; G01N 2030/8813; G01N 2333/47; G01N 2333/4716; G01N 2333/974; G01N 2800/2814; G01N 2030/8868; G01N 2333/4712; G01N 30/08; G01N 33/6848; G01N 2030/8831; C07K 14/47
See application file for complete search history.

(56) References Cited

U.S. PATENT DOCUMENTS

| | | | | |
|---|---|---|---|---|
| 2013/0337479 | A1* | 12/2013 | Uchida | G01N 33/6896 530/382 |
| 2016/0178643 | A1* | 6/2016 | Everett | C12Q 1/6883 435/7.92 |

FOREIGN PATENT DOCUMENTS

| | | |
|---|---|---|
| EP | 1 451 590 A1 | 9/2004 |
| JP | 2005-511063 A | 4/2005 |
| JP | 2006-284389 A | 10/2006 |
| JP | 2006-308533 A | 11/2006 |
| JP | 2010-071900 A | 4/2010 |
| JP | 2016-028244 A | 2/2016 |
| WO | 03/048775 A2 | 6/2003 |

OTHER PUBLICATIONS

Written Opinion for PCT/JP2018/026582, dated Oct. 2, 2018.
International Search Report for PCT/JP2018/026582, dated Oct. 2, 2018.
International Preliminary Report on Patentability for PCT/JP2018/026582, dated Jan. 14, 2020.
Notification Concerning Transmittal of International Preliminary Report on Patentability for PCT/JP2018/026582, dated Jan. 23, 2020.
Communication dated Dec. 16, 2021 from the Chinese Patent Office in Chinese Application No. 201880059582.7.
Lan Zhu et al., "The Role of Dipeptidyl Peptidase IV in the Cleavage of Glucagon Family Peptides", The Journal of Biological Chemistry, 2003, vol. 278, No. 25, pp. 22418-22423 (6 pages total).

* cited by examiner

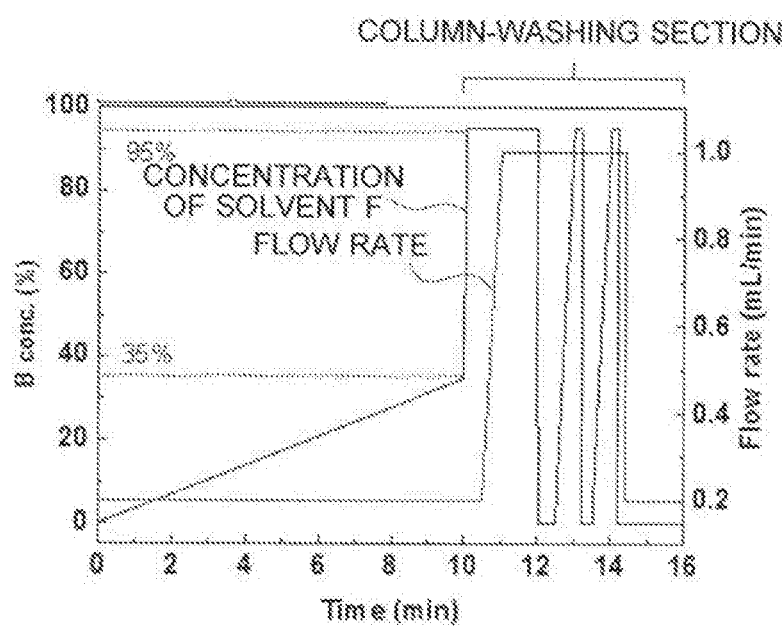

Fig. 4

| Peptide ID | Precursor (m/z) | Product (m/z) | Q1 Pre Rod Bias (V) | CE (V) | Q3 Pre Rod Bias (V) | Type |
|---|---|---|---|---|---|---|
| AD1008 | 646.05 | 763.95 | -34.0 | -26.0 | -28.0 | Quantifier |
| | 646.05 | 410.25 | -24.0 | -24.0 | -15.0 | Qualifier |
| | 646.05 | 616.35 | -34.0 | -26.0 | -22.0 | Qualifier |
| AD1025 | 538.95 | 534.25 | -28.0 | -21.0 | -20.0 | Quantifier |
| | 538.95 | 484.75 | -40.0 | -21.0 | -14.0 | Qualifier |
| | 538.95 | 541.25 | -28.0 | -18.0 | -20.0 | Qualifier |
| AD1042 | 520.75 | 449.70 | -26.0 | -19.0 | -16.0 | Quantifier |
| | 520.75 | 401.20 | -26.0 | -25.0 | -20.0 | Qualifier |
| | 520.75 | 801.40 | -26.0 | -27.0 | -30.0 | Qualifier |
| AD1046 | 856.90 | 720.25 | -20.0 | -30.0 | -20.0 | Quantifier |
| | 856.90 | 993.55 | -26.0 | -29.0 | -30.0 | Qualifier |
| | 856.90 | 555.35 | -20.0 | -29.0 | -20.0 | Qualifier |
| AD1048 (ADPEP2036) | 776.00 | 1061.50 | -40.0 | -18.0 | -40.0 | Quantifier |
| | 776.00 | 1036.45 | -22.0 | -22.0 | -38.0 | Qualifier |
| | 776.00 | 1150.50 | -40.0 | -23.0 | -34.0 | Qualifier |
| AD1049 | 512.30 | 518.30 | -26.0 | -20.0 | -26.0 | Quantifier |
| | 512.30 | 629.35 | -26.0 | -20.0 | -32.0 | Qualifier |
| | 512.30 | 453.75 | -26.0 | -17.0 | -23.0 | Qualifier |
| ADPEP109315 | 518.25 | 642.85 | -20.0 | -16.0 | -22.0 | Quantifier |
| | 518.25 | 586.30 | -26.0 | -19.0 | -34.0 | Qualifier |
| | 776.90 | 796.40 | -30.0 | -28.0 | -28.0 | Qualifier |
| ADPEP421488 | 725.40 | 378.15 | -28.0 | -16.0 | -19.0 | Quantifier |
| | 725.40 | 917.45 | -22.0 | -23.0 | -34.0 | Qualifier |
| | 725.40 | 873.95 | -22.0 | -23.0 | -20.0 | Qualifier |
| ADPEP1315 | 744.35 | 885.45 | -30.0 | -23.0 | -34.0 | Quantifier |
| | 744.35 | 757.40 | -22.0 | -34.0 | -28.0 | Qualifier |
| | 496.60 | 472.25 | -15.0 | -27.0 | -25.0 | Qualifier |
| ADPEP12neu | 942.00 | 449.20 | -28.0 | -30.0 | -22.0 | Quantifier |
| | 628.35 | 449.20 | -32.0 | -16.0 | -22.0 | Qualifier |
| | 942.00 | 547.25 | -22.0 | -27.0 | -20.0 | Qualifier |
| ADPEP1396 | 781.35 | 761.40 | -22.0 | -14.0 | -28.0 | Quantifier |
| | 521.25 | 533.30 | -26.0 | -20.0 | -20.0 | Qualifier |
| | 781.35 | 1072.50 | -22.0 | -30.0 | -32.0 | Qualifier |
| ADPEP1039 | 638.80 | 1072.50 | -32.0 | -21.0 | -32.0 | Quantifier |
| | 638.80 | 862.40 | -32.0 | -25.0 | -24.0 | Qualifier |
| | 638.80 | 747.35 | -24.0 | -28.0 | -28.0 | Qualifier |
| ADPEP1250 | 478.25 | 462.25 | -23.0 | -23.0 | -16.0 | Quantifier |
| | 478.25 | 509.75 | -25.0 | -19.0 | -26.0 | Qualifier |
| | 478.25 | 351.20 | -24.0 | -23.0 | -10.0 | Qualifier |
| AD1089 | 458.25 | 331.20 | -24.0 | -24.0 | -12.0 | Quantifier |
| | 458.25 | 602.35 | -17.0 | -20.0 | -22.0 | Qualifier |
| | 458.25 | 761.40 | -24.0 | -22.0 | -26.0 | Qualifier |

SEQUENCE LISTING

```
<160> NUMBER OF SEQ ID NOS: 14

<210> SEQ ID NO 1
<211> LENGTH: 17
<212> TYPE: PRT
<213> ORGANISM: Homo sapiens

<400> SEQUENCE: 1

Ala Pro Leu Gln Pro Val Thr Pro Leu Gln Leu Phe Glu Gly Arg Arg
1               5                   10                  15

Asn

<210> SEQ ID NO 2
<211> LENGTH: 16
<212> TYPE: PRT
<213> ORGANISM: Homo sapiens

<400> SEQUENCE: 2

Pro Gly Arg Gln Ser Gln Glu Gly Ala Gly Leu Pro Ser His His Gly
1               5                   10                  15
```

-continued

```
<210> SEQ ID NO 3
<211> LENGTH: 11
<212> TYPE: PRT
<213> ORGANISM: Homo sapiens

<400> SEQUENCE: 3

Ala Ala Pro Pro Gly Ala Glu Gly Asn Arg Thr
1               5                   10

<210> SEQ ID NO 4
<211> LENGTH: 17
<212> TYPE: PRT
<213> ORGANISM: Homo sapiens

<400> SEQUENCE: 4

Lys Leu Ala Glu Leu Pro Ala Ala Ala Gln Pro Ser Ala Glu Asp Ser
1               5                   10                  15

Asp

<210> SEQ ID NO 5
<211> LENGTH: 21
<212> TYPE: PRT
<213> ORGANISM: Homo sapiens

<400> SEQUENCE: 5

Thr Ala Thr Ser Glu Tyr Gln Thr Phe Phe Asn Pro Arg Thr Phe Gly
1               5                   10                  15

Ser Gly Glu Ala Asp
            20

<210> SEQ ID NO 6
<211> LENGTH: 14
<212> TYPE: PRT
<213> ORGANISM: Homo sapiens

<400> SEQUENCE: 6

Ala Pro Val Ile His Gln Glu Met Ile Gly Gly Leu Arg Asn
1               5                   10

<210> SEQ ID NO 7
<211> LENGTH: 16
<212> TYPE: PRT
<213> ORGANISM: Homo sapiens

<400> SEQUENCE: 7

Gln Thr Ala Ser Gly Gln Ala Leu Lys Gly Asp Gly Gly Leu Tyr Ser
1               5                   10                  15

<210> SEQ ID NO 8
<211> LENGTH: 20
<212> TYPE: PRT
<213> ORGANISM: Homo sapiens

<400> SEQUENCE: 8

Gly Leu Gly Leu Ser Tyr Leu Ser Ser His Ile Ala Asn Val Glu Arg
1               5                   10                  15

Val Pro Phe Asp
            20

<210> SEQ ID NO 9
<211> LENGTH: 14
<212> TYPE: PRT
<213> ORGANISM: Homo sapiens
```

```
<400> SEQUENCE: 9

Arg Ser Gly Gly Asn Ala Thr Leu Gln Val Asp Ser Trp Pro
1               5                   10

<210> SEQ ID NO 10
<211> LENGTH: 19
<212> TYPE: PRT
<213> ORGANISM: Homo sapiens

<400> SEQUENCE: 10

Asn Ile Ala Ile Val Gly Asp Val Arg Leu Val Gly Glu Val Pro Ser
1               5                   10                  15

Ser Gly Thr

<210> SEQ ID NO 11
<211> LENGTH: 13
<212> TYPE: PRT
<213> ORGANISM: Homo sapiens

<400> SEQUENCE: 11

Thr Ala Thr Ser Glu Tyr Gln Thr Phe Phe Asn Pro Arg
1               5                   10

<210> SEQ ID NO 12
<211> LENGTH: 12
<212> TYPE: PRT
<213> ORGANISM: Homo sapiens

<400> SEQUENCE: 12

Gly Leu Asp Glu Asp Ser Asp Arg Ala Ile Glu Gly
1               5                   10

<210> SEQ ID NO 13
<211> LENGTH: 13
<212> TYPE: PRT
<213> ORGANISM: Homo sapiens

<400> SEQUENCE: 13

Gly Leu Asp Glu Asp Ser Asp Arg Ala Ile Glu Gly Arg
1               5                   10

<210> SEQ ID NO 14
<211> LENGTH: 14
<212> TYPE: PRT
<213> ORGANISM: Homo sapiens

<400> SEQUENCE: 14

Gly Val Ser Gly Ser His Phe Val Gly Val Asp Gly Val Arg
1               5                   10
```

DISEASE DETECTION METHOD

CROSS REFERENCE TO RELATED APPLICATIONS

This application is a National Stage of International Application No. PCT/JP2018/026582 filed Jul. 13, 2018, claiming priority based on Japanese Patent Application No. 2017-137724 filed Jul. 14, 2017.

TECHNICAL FIELD

The present invention relates to a method for detecting a specific disease based on a measured value of the amount of a specific component contained in a biological sample, such as blood or urine. More specifically, the present invention relates to a detection method for the disease of cognitive dysfunction.

BACKGROUND ART

A substance which is present in the blood, urine or other types of biological samples collected from patients suffering from a specific disease and yet is not present or barely present in the biological samples collected from other individuals can serve as a biomarker, i.e. a substance which indicates that those patients are affected with the disease in question. Accordingly, it has been a common practice to measure the amounts of substances serving as biomarkers contained in biological samples, and diagnose various kinds of disease from the measured results. For the measurements of biomarkers in biological samples, in-vitro diagnostics have been commonly used.

One of the measurement methods for biomarkers using in-vitro diagnostics is a method which utilizes an antigen-antibody interaction for a measurement of a specific protein or peptide contained in a biological sample which is either in its original form or in a previously diluted form. For example, in an enzyme-linked immunosorbent assay (ELISA) or chemiluminescent immunoassay (CLIA), a specific protein or peptide in a sample is made to be linked with a primary or secondary antibody labeled with an enzyme which develops a color upon reacting with a substrate, and the amount of protein or peptide is determined from the amount of color development of the antibody binding to the protein or peptide. In the case of a radioimmunoassay (RIA), the primary or secondary antibody is labeled with a radioisotope, and the amount of specific protein or peptide is determined from the amount of radiation from the antibody binding to protein or peptide. In the case where the specific protein (or the like) is an enzyme, an enzyme activity measurement method is used which includes the steps of making the protein react with the substrate and determining the amount of product resulting from the reaction.

In recent years, it has been progressively revealed that a protein which exists in a complete form in a living organism when the living organism is in normal conditions (such a protein is hereinafter called the "intact protein") produces various types of partial peptides (or partial proteins) which are formed by digestion when the living organism is affected with a specific disease ("disease state"), or that partial peptides or partial proteins of the intact protein are synthesized through translation due to splicing abnormality or other problems in the translational synthesis of the protein when the living organism is in the disease state. It has also been progressively revealed that, in the disease state, the amount and kind of partial protein or partial peptide formed by digestion or synthesized through translation changes with the progress of the disease. Accordingly, attempts have been made to search for a method for diagnosing the disease as well as determining its progress from not only the amount of intact protein in the biological sample but also the kind of intact protein as well as the amounts and kinds of partial proteins or partial peptides originating from that intact protein. However, any of those aforementioned conventional measurement methods which employ an antigen-antibody interaction or enzyme-substrate reaction measures each individual protein or peptide. Therefore, it requires a considerable amount of time and labor to individually perform measurements for an intact protein and its partial proteins or partial peptides. Furthermore, an increase in the number of measurement targets requires a corresponding increase in the amount of biological sample to be collected from each subject (a person affected with the disease).

To address those problems, a method has been proposed in which the amounts of proteins in a biological sample as well as those of their partial proteins or partial peptides are exhaustively determined with a liquid chromatograph mass spectrometer. Then, the disease is diagnosed based on the presence pattern and/or profile of the proteins, partial proteins and partial peptides. For example. Patent Literature 1 describes a method for detecting a non-alcoholic liver disease (including non-alcoholic steatohepatitis) from the result of a measurement using a mass spectrometer for a protein and its partial peptides which show a difference in terms of the presence/absence and the abundance between healthy individuals and the patients with non-alcoholic fatty liver diseases, or between the fatly liver and the patients with the non-alcoholic steatohepatitis. Patent Literatures 2 and 3 each describe a method for detecting a liver cancer from the result of a measurement using a mass spectrometer for a protein and its partial peptides which show a difference in terms of the presence/absence and the abundance between healthy individuals and liver cancer patients.

CITATION LIST

Patent Literature

Patent Literature 1: JP 2010-071900 A
Patent Literature 2: JP 2006-308533 A
Patent Literature 3: JP 2006-284389 A

SUMMARY OF INVENTION

Technical Problem

Biological samples used for disease diagnosis are collected from the subjects at various hospitals, health clinics or other medical institutions. It is difficult to collect biological samples by the same procedure, under the same conditions and with the same level of quality at all institutions. Therefore, even a peak originating from the same protein may vary in its signal intensity due to the difference in the procedure, conditions, quality and other factors related to the collection of the biological samples.

The diagnosis of a disease or its progress is made, for example, based on the result of an analysis of the amount, abundance ratio (quantitative ratio) and other aspects of an intact protein as well as its partial proteins and partial peptides. Therefore, if there is a variation in signal intensity of the peaks of the respective components, a change occurs not only in the respective amounts of the protein, partial proteins and partial peptides but also in the quantitative ratio of the protein, partial proteins and partial peptides, so that it is impossible to make a correct diagnosis.

It should be noted that, in the previous description, a portion of an intact protein has been called a "partial protein" or "partial peptide" for convenience, although a portion of a protein is normally called a "peptide".

The problem to be solved by the present invention is to provide a technique for performing a correct measurement using a mass spectrometer for a peptide which serves as a biomarker for a specific disease.

Solution to Problem

A disease detection method according to the present invention developed for solving the previously described problem is a method for detecting a specific disease based on the result of a measurement in which the amount of a peptide serving as a hiomarker contained in a biological sample is determined by using a chromatograph mass spectrometer, in which a pretreatment process performed before the measurement using the chromatograph mass spectrometer includes the steps of:

a) preparing a mixed sample solution by adding a stable isotope reagent and a trifluoroacetic acid to the biological sample, where the stable isotope reagent is prepared beforehand by labeling the peptide with a stable isotope;

b) boiling the mixed sample solution;

c) injecting the mixed sample solution after boiled into a solid-phase extraction column to make the peptide be retained in the solid-phase extraction column; and d) passing a water-soluble organic solvent through the solid-phase extraction column to elute the peptide retained in the solid-phase extraction column and collect the eluate.

Examples of the biological sample include blood, plasma, serum, cerebral fluid and urine.

The peptide serving as a hiomarker is a peptide whose abundance in a biological sample collected from a patient affected with a specific disease is significantly different from its abundance in a biological sample collected from an individual who is not affected with that specific disease. For example, a peptide can serve as a biomarker if the peptide takes the form of an intact protein in a living organism which is not affected with a specific disease, while the peptide is produced or synthesized as a portion of the intact protein in a living organism which is affected with that specific disease.

The stable isotope reagent prepared by labeling the peptide with a stable isotope is formed by replacing one or more of the atoms forming the peptide with the stable isotopic elements of those atoms.

The trifluoroacetic acid added to the biological sample in the pretreatment process has the effect of separating an entangled peptide from a matrix of fibrinogen, albumin and other substances in the biological sample. The step of boiling the mixed sample solution has the effect of loosening a peptide if the peptide is in an aggregated form. The period of time to boil the mixed sample solution should preferably be within, but is not limited to, a range from 1 minute to 30 minutes. For example, it is preferable to set an appropriate boiling time according to the kind of biological sample and/or the kind of biomarker (peptide) which is the target of the mass spectrometry.

The stable isotope reagent added to the biological sample has approximately the same value of the mass-to-charge ratio as the corresponding peptide, and is also similar in physical/chemical nature to the peptide concerned. Accordingly, the stable isotope reagent and the corresponding peptide behave in a similar manner when the biological sample is subjected to a measurement with a chromatograph mass spectrometer. A peak of the stable isotope reagent and a peak of the corresponding peptide appear close to each other on the mass spectrum obtained as a result of a chromatograph mass spectrometric analysis. If there is a variation in the yield of the pretreatment process, the variation affects both the peak of the stable isotope reagent and that of the corresponding peptide, Since the amount of added stable isotope reagent is previously known, it is possible to accurately determine the quantity of a peptide by comparing the peak intensities of the two substances.

If the water-soluble organic solvent is 50%400% methanol, it is preferable for the present invention to further include the following steps after the eluting step:

evaporating the water-soluble organic solvent contained in the eluate to obtain the peptide in a dried form; and preparing a sample solution for mass spectrometry by dissolving the dried peptide in an aqueous solution containing 0.1%4% trifluoroacetic acid and 5%-50% acetonitrile.

In a preferable mode of the present invention, the water-soluble organic solvent contains 0.1%-1% trifluoroacetic acid and 10%-99.9% acetonitrile, and when the concentration of the acetonitrile is within a range of 50%-99.9%, a step of preparing a sample solution for mass spectrometry by diluting the eluate so that the concentration of the acetonitrile contained in the eluate becomes lower than 50% is additionally performed after the eluting step.

It should be noted that the "%" symbol used for expressing the concentrations of various substances in the present description means "v/v %".

In the case of using methanol to elute the peptide from the solid-phase extraction column, if the eluate is directly supplied to the chromatograph mass spectrometer, it is necessary to evaporate the methanol since the methanol may possibly prevent the separation of the biological sample. By comparison, in the case of performing the elution using a water-soluble organic solvent containing 0.1%-1% trifluoroacetic acid and 10%-99.9% acetonitrile, the process of evaporating the water-soluble organic solvent can be omitted. However, if the concentration of the acetonitrile is within a range of 50%-99.9%, the acetonitrile prevents the separation, and it is therefore preferable to dilute the eluate so that the concentration of the acetonitrile becomes lower than 50%, and use the diluted eluate as the sample solution for mass spectrometry.

In a further preferable mode, the chromatograph truss spectrometer includes a liquid chromatograph unit and a mass spectrometer unit capable of a multiple reaction monitoring (MRM) measurement, and the measurement using the chromatograph mass spectrometer includes the steps of:

temporally separating the sample solution for mass spectrometry in the liquid chromatograph unit; and performing an MRM measurement in the mass spectrometer unit under measurement conditions including a plurality of MRM transitions corresponding to the combinations of a precursor ion generated by the ionization of the peptide contained in the sample solution for mass spectrometry temporally separated in the liquid chromatograph unit and a plurality of kinds of product ions formed from the precursor ion by the fragmentation of amino acids at different locations in the precursor ion.

One type of disease to be detected by the disease detection method according to the present invention is a disease which causes a situation in which a protein that will be an intact protein when in normal conditions will be generated or synthesized as a portion of that intact protein when in a specific state of disease. Examples of such a disease include the disease of cognitive dysfunction as well as liver diseases (non-alcoholic fatty liver diseases, fatty liver and liver cancer). In the case where the specific disease is the disease of cognitive dysfunction, the intact protein may be prothrombin, gelsolin, complement C4A or complement C3. There are also other kinds of proteins included in the intact protein, such as the transcription factor AP-2 gamma, oxytocin receptor, E3 ubiquitin-protein ligase HERC2, tumor necrosis factor receptor superfamily member 16, neurexin-2-beta precursor, neurexin 1-β and protocadherin gamma A-10.

Advantageous Effects of Invention

According to the present invention, a mixed sample solution is prepared by adding trifluoroacetic acid to a biological sample and is subsequently boiled. By such a process, the peptide can be separated from a matrix (fibrinogen, albumin and other substances) in the biological sample, and the peptide in an aggregate form can be loosened. Therefore, when the mixed sample solution is injected into the solid-phase extraction column, the peptide in the biological sample can be retained in the solid-phase extraction column in a stable manner. Accordingly, the peptide retained in the solid-phase extraction column can subsequently be eluted by passing a water-soluble organic solvent through the solid-phase extraction column.

Since the stable isotope reagent of the peptide serving as a biomarker is added to the biological sample, an accurate quantity of the peptide can be determined from the data obtained by performing a chromatograph mass spectrometric analysis on the biological sample.

BRIEF DESCRIPTION OF DRAWINGS

FIG. 3 is a diagram showing a gradient profile for an analysis in the liquid chromatograph unit.

FIG. 4 is a table showing MRM transitions of biomarker peptides for 14 kinds of the disease of cognitive dysfunction.

DESCRIPTION OF EMBODIMENTS

One embodiment of the disease detection method according to the present invention is hereinafter described with reference to the drawings.

Figure 1:
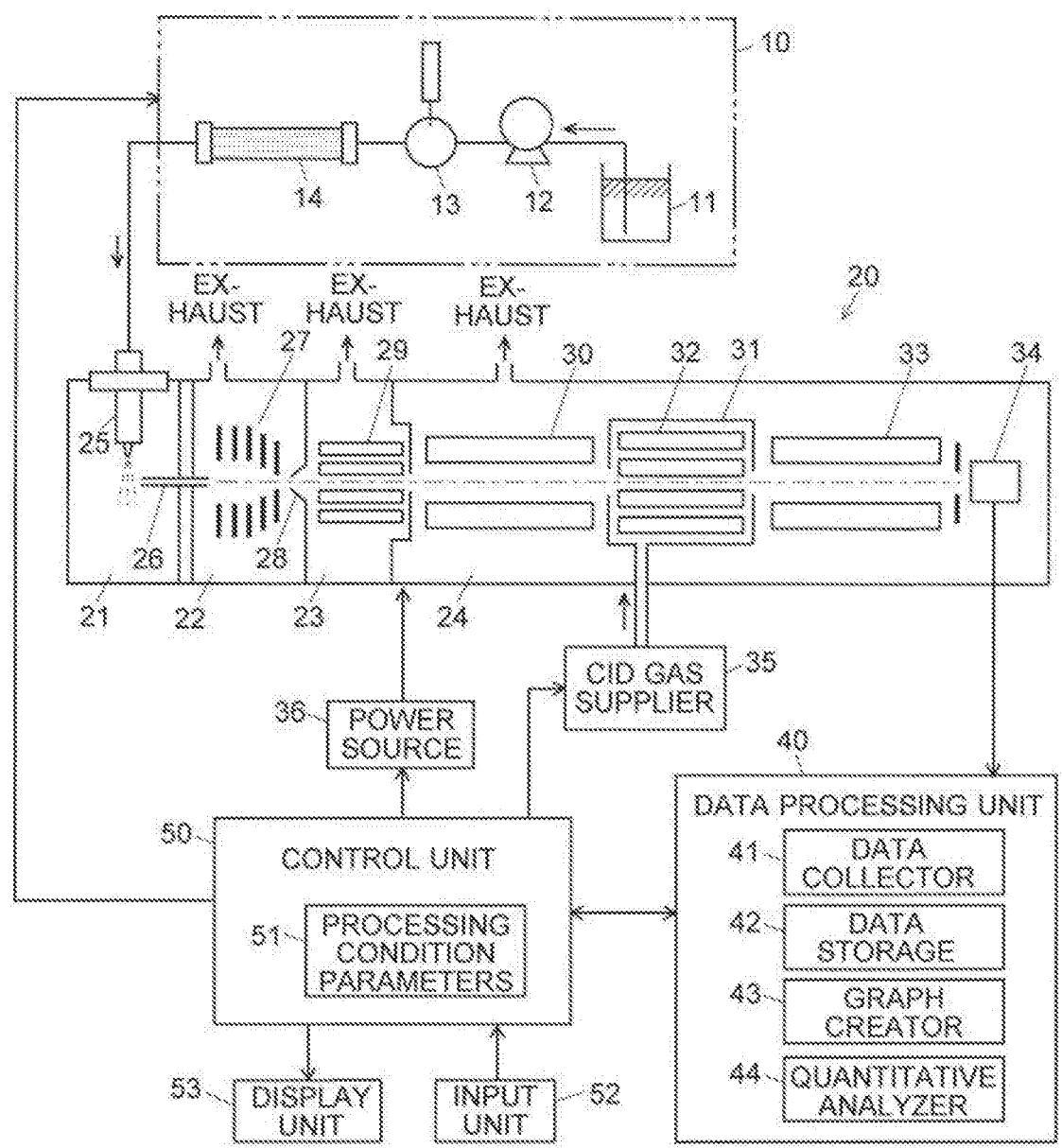
FIG. 1 is a schematic configuration diagram of one embodiment of the mass spectrometer to be used for carrying oust the disease detection method according to the present invention.

FIG. 1 is a schematic configuration diagram of a liquid chromatograph mass spectrometer (LC-MS/MS) to be used for carrying out the disease detection method according to the present invention.

The liquid chromatograph mass spectrometer includes a liquid chromatograph unit (LC unit) 10 and a mass spectrometer unit (MS/MS unit) 20.

The LC unit 10 includes: a mobile phase container 11 in which a mobile phase is stored: a pump 12 configured to draw the mobile phase and supply it at a constant flow rate; an injector 13 configured to inject a predetermined amount of each prepared sample into the mobile phase; and a column 14 configured to separate various compounds in the sample in the temporal direction. Two or more mobile phase containers 11 and pumps 12 will be provided in the case where the LC unit 10 is configured to perform a so-called gradient separation and separate the compounds contained in the sample while continuously changing the composition of a plurality of mobile phases.

The MS/MS unit 20 is a tandem quadrupole mass spectrometer and is configured as a multistage differential pumping system including an ionization chamber 21 maintained at atmospheric pressure and an analysis chamber 24 evacuated to a high degree of vacuum by a high-performance vacuum pump (not shown), between which first and second intermediate vacuum chambers 22 and 23 are provided having their degrees of vacuum increased in a stepwise manner. The ionization chamber 21 has an electrospray ionization probe 25 configured to spray a sample solution while imparting electric charges to the sample solution. The ionization chamber 21 and the first intermediate vacuum chamber 22 in the next stage communicate with each other through a thin heated capillary 26. The first intermediate vacuum chamber 22 is separated from the second intermediate vacuum chamber 23 by a skimmer 28 having a small hole at its apex. Ion guides 27 and 29 configured to transport ions to the next stage while converging them are respectively placed within the first and second intermediate vacuum chambers 22 and 23. The analysis chamber 24 contains a front quadrupole mass filter 30 which separates ions according to their mass-to-charge ratios and a rear quadrupole mass filter 33 which also separates ions according to their mass-to-charge ratios, with a collision cell 31 containing a multipole ion guide 32 placed between the two filters, as well as an ion detector 34. A CID gas supplier 35 is configured to supply CID gas (e.g. argon or nitrogen) into the collision cell 31. A power source 36 is configured to apply predetermined voltages to the electrospray ionization probe 25, ion guides 27, 29 and 32, quadrupole mass filters 30 and 33, as well as other relevant sections, respectively.

The data processing unit 40 includes a data collector 41, data storage section 42, graph creator 43, quantitative analyzer 44 and other components as its functional blocks. A control unit 50, which is equipped with an input unit 52 and a display unit 53, includes a processing condition parameter storage section 51. Based on the processing condition parameters previously stored in this storage section 51, the control unit 50 controls the operations of the pump 12 and injector 13 in the liquid chromatograph unit 10 as well as the power source 36, CID gas supplier 35 and other components in the mass spectrometer unit 20. At least some of the functions of the control unit 50 and the data processing unit 40 can be realized by using a personal computer as a hardware resource and executing, on the personal computer, dedicated controlling and processing software previously installed on the same computer.

A basic operation of the MS/MS measurement in the LC-MS/MS according to the present embodiment is as follows:

The pump 12 draws a mobile phase from the mobile phase container 11 and supplies it to the column 14 at a constant flow rate. A predetermined amount of sample solution is introduced from the injector 13 into the mobile phase. The injected sample is carried into the column 14 by the flow of the mobile phase. While the sample is passing through the column 14, the various compounds in the sample separated from each other in the temporal direction and exit from the outlet port of the column 14, to be introduced into the MS/MS unit 20.

In the MS/MS unit 20, the eluate from the column 14 arrives at the electrospray ionization probe 25, whereupon the eluate is sprayed from the probe 25 while receiving electric charges at the tip of the probe 25. The electrically charged droplets formed by the spraying are progressively divided into finer droplets by the electrostatic force due to the imparted electric charges. The solvent is vaporized through this process, and the ions originating from the compounds are ejected.

The ions generated in this manner are sent through the heated capillary 26 into the first intermediate vacuum chamber 22, in which the ions are converged by the ion guide 27 and sent through the small hole at the apex of the skimmer 28 into the second intermediate vacuum chamber 23. The ions originating from the compounds are converged by the ion guide 29 and sent into the analysis chamber 24, in which the ions are introduced into the longitudinally extending space in the front quadrupole mass filter 30. It should be naturally understood that the ionization method is not limited to the electrospray ionization. Other methods may also be used, such as the atmospheric pressure chemical ionization or atmospheric pressure photoionization.

When an MS/MS analysis is performed in the MS/MS unit 20, a predetermined voltage (generated by superposing a radio-frequency voltage on a direct voltage) is applied from the power source 36 to each rod electrode in the front quadrupole mass filter 30 and the rear quadrupole mass filter 33. Meanwhile, CID gas is continuously or intermittently supplied from the CID gas supplier 35 into the collision cell 31. Among the various kinds of ions sent into the front quadrupole mass filter 30, only an ion having a specific mass-to-charge ratio corresponding to the voltages applied to the rod electrodes of the front quadrupole mass filter 30 is allowed to pass through the same filter 30 and be introduced into the collision cell 31 as a precursor ion. Within the collision cell 31, the precursor ion collides with the CID gas and is fragmented into various kinds of product ions. The generated product ions are introduced into the rear quadrupole mass filter 33. Among those ions, only an ion having a specific mass-to-charge ratio corresponding to the voltages applied to the rod electrodes of the rear quadrupole mass filter 33 is allowed to pass through the same filter 33, to eventually arrive at and be detected by the ion detector 34. A pulse-counting detector can be used as the ion detector 34, in which case the ion detector 34 generates, as the detection signals, a number of pulse signals corresponding to the number of incident ions.

The detection signals of the ion detector 34 are sent to the data processing unit 40, which creates mass spectra and mass chromatograms as well as executes the processing for analyzing those mass spectra and mass chromatograms.

Based on the result of the analysis, a diagnosis is made as to whether or not the subject who is the provider of the biological sample is affected with a specific disease. If the subject has been found to be affected with the specific disease, its progress is also determined.

As with a commonly used LC-MS/MS, the following modes are available for the NIS/NIS measurement in the present embodiment: the multiple reaction monitoring (MRM) measurement, product ion scan measurement, precursor ion scan measurement, and neutral loss scan measurement.

In the MRM measurement, the MS/MS measurement is performed by operating each of the front and rear quadrupole mass filters 30 and 33 so that only an ion having a predetermined mass-to-charge ratio is allowed to pass through the filter. By such an operation, a specific product ion corresponding to a specific precursor ion originating from the target compound is detected. The MRM measurement allows for the setting of a plurality of measurement channels each of which is defined by the combination of one mass-to-charge ratio (m/z) of the precursor ion and one mass-to-charge ratio (m/z) of the product ion. The combination of one mass-to-charge ratio of the precursor ion and one mass-to-charge ratio of the product ion is called, the "MRM transition". In the disease detection method which will be hereinafter described, the MRM measurement is used as the NIS/NIS measurement.

A measurement processing carried out by using the previously described LC-MS/MS to detect a specific disease is hereinafter described. The following description deals with the example of the measurement processing to be performed for detecting the disease of cognitive dysfunction.

<1. Preparation of Reagents, Tools and Other Required Items>

The following reagents, tools and other required items are prepared.

(1) Standard Solution for Calibration Curve (STD Solution): A reagent which contains one or more peptides, each in a predetermined quantity, where each peptide is a portion of the amino acid sequence of an intact protein which can serve as a biomarker for the disease of cognitive dysfunction (prothrombin, gelsolin, complement C4A or complement C3). Specifically, the peptide or peptides are selected from the 14 kinds of peptides listed in Table 1. As an alternative, a standard serum containing one or more peptides each in a predetermined quantity may also be used. The STD solution is diluted with a predetermined dilution liquid in a stepwise manner to prepare a solution for each calibration point on the calibration curve (e.g. six solutions for six calibration points), Table 1 lists the 14 kinds of peptides, showing the sequence number (Nos. 1-14), identification number (ID), name of the protein from which the peptide originates, and amino acid sequence of the peptide.

TABLE 1

| No. | Peptide ID | Name of Protein | Amino Acid Sequence |
|---|---|---|---|
| 1 | AD1008 | Complement C4-A | APLQPVTPLQLFEGRRN |
| 2 | AD1025 | Transcription factor AP-2 gamma | PGRQSQEGAGLPSHHG |
| 3 | AD1042 | Oxytocin receptor | AAPPGAEGNRT |
| 4 | AD1046 | E3 ubiquitin-protein linse HERC2 | KLAELPAAAQPSAEDSD |
| 5 | AD1048 (ADPEP2036) | Prothrombin | TATSEYQTFFNPRTFGSGEAD |

TABLE 1-continued

| No. | Peptide ID | Name of Protein | Amino Acid Sequence |
|---|---|---|---|
| 6 | AD1049 | Complement C3 | APVIHQEMIGGLRN |
| 7 | ADPEP109315 | Tumor necrosis factor receptor superfamily member 16 | QTASGQALKGDGGLYS |
| 8 | ADPEP421488 | Gelsolin | GLGLSYLSSHIANVERVPFD |
| 9 | ADPEP1315 | Neurexin-2-beta precursor | RSGGNATLQVDSWP |
| 10 | ADPEP12neu | Neurexin 1-β | NIAIVGDVRLVGEVPSSGT |
| 11 | ADPEP1396 | Prothrombin precursor | TATSEYQTFFNPR |
| 12 | ADPEP1039 | Prothrombin precursor | GLDEDSDRAIEG |
| 13 | ADPEP1250 | Prothrombin precursor | GLDEDSDRAIEGR |
| 14 | AD1089 | Protocadherin gamma A-10 | GVSGSHFVGVDGVR |

(2) Standard Solution for Accuracy Control (QC Solution): A solution prepared by mixing the solutions for calibration points prepared from the STD solution. For example, in the case of six calibration points, three mixed solutions are prepared as QC solutions, including the first one prepared by mixing the solution for calibration point 1 and the solution for calibration point 2, the second one prepared by mixing the solution for calibration point 3 and the solution for calibration point 4, and the third one prepared by mixing the solution for calibration point 5 and the solution for calibration point 6, (3) Stable Isotope Reagent: A reagent containing the 14 kinds of peptides, each in a predetermined quantity, with some of the atoms of the peptides replaced by stable isotopes.

(4) Solvent A: water-soluble organic solvent containing 0.1%-1% TFA and 5%-50% acetonitrile (ACN)

(5) Solvent B: 50%-100% methanol (6) Solvent C: aqueous solution containing 0.1%-1% TFA (7) Solvent D: water-soluble organic solvent containing 0.1%-1% TFA and 5%-50% methanol (8) Aluminum seal (9) Sample plate with 96 wells

(10) Plate mat for preventing vaporization

<2. Preparation of Biological Sample (Serum)>

A blood specimen is collected from a subject. After being placed for a predetermined period of time, the blood is subjected to centrifugal separation to collect supernatant (serum)

<3. Preparation of Sample>

Figure 2:
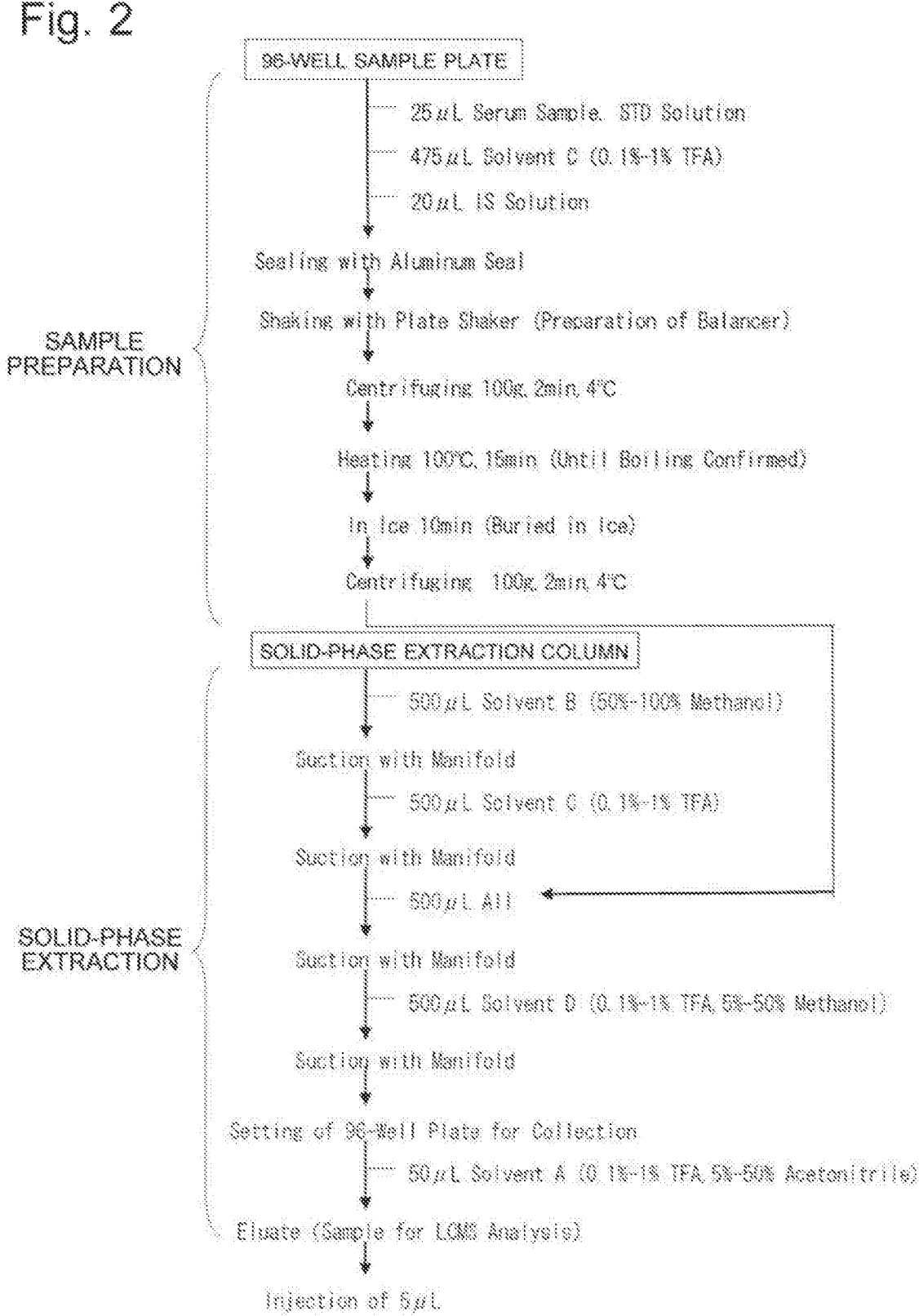
FIG. 2 is a chart for explaining the procedure of the pretreatment.

A pretreatment is performed according to the procedure n in FIG. 2.

The serum as the biological sample is injected into each well of the 96-well sample plate, 25 μL in each well. The STD solution and QC solutions, 25 μL each, are individually dropped in wells which are different from those into which the serum has been injected.

Next, 475 μL of solvent C (aqueous solution containing 0.1%-1% TFA) is added to each of the wells of the sample plate into which the serum, STD solution and QC solutions have been injected. Furthermore, 20 μL of the stable isotope reagent is added to each of those wells. A total of 520 μL of (mixed) liquid is consequently held in each well.

Subsequently, the top surface of the sample plate is sealed with the aluminum seal. The sealed sample plate is shaken with a plate shaker. After the shaking, the following operations are successively performed, using a centrifuge compatible with the sample plate: first centrifugal separation (100 g; 2 min.; 4° C.), heat treatment (100° C. 15 min.), storage in ice (10 min.) and second centrifugal separation (100 g; 2 min.; 4° C.).

<4. Processing Using Solid-Phase Extraction Column (Solid-Phase Extraction Plate)>

Solvent B (500 μL of 50%-100% methanol) is passed through each well of a solid-phase extraction column (trade name: Oasis HLB μElution Plate, manufactured by Waters Corporation) compatible with the 96-well plate (this column is hereinafter called the "solid-phase extraction plate") to remove insoluble components. Subsequently, 500 μL of solvent C (aqueous solution containing 0.1%-1% TFA) is passed to prepare solid-phase extraction plate.

Next, 500 μL of the supernatant held in each well of the sample plate which has been subjected to the second centrifugal separation in the pretreatment is passed through the corresponding well of the solid-phase extraction plate. Subsequently, 500 μL of solvent D (water-soluble organic solvent containing [0.1%-1% TEA]+[5%-50% methanol]) is passed through each well of the solid-phase extraction plate to wash off matrix components non-specifically adsorbed on the solid-phase extraction plate. Subsequently, 50 μL of solvent A (water-soluble organic solvent containing [0.1%-1% TFA]+[5%-50% ACN]) is added to each well of the solid-phase extraction plate to elute the peptides adsorbed on the solid-phase extraction plate into each well of the 96-well sample plate for mass spectrometry. The solution obtained in this manner in each well of the 96-well sample plate is the sample solution for mass spectrometry.

<5. Measurement by Chromatograph Mass Spectrometer>

The 96-well sample plate holding the sample solution for mass spectrometry obtained by the processing using the solid-phase extraction column was set on a sample placement section in the injector 13 of the LC-MS/MS, and a chromatograph mass spectrometric analysis was carried out. The specific names of the devices used as the LC unit 10 and MS/MS unit 20, as well as the processing conditions and other related items of information are shown below, along with the result of the analysis.

<5.1 LC Unit>

Device Name: A high-performance liquid chromatograph (trade name: Nexera XR, manufactured by Shimadzu Corporation) capable of gradient analysis was used.

Column: A reversed phase column designed for analyzing peptides or proteins (trade name: Aeris® peptide, manufactured by Phenomenex Inc., measuring 2.1×50 mm and 2.6 µm, with the maximum pressure of 1000 bar, or 100 MPa), was used.

Analysis Method: A gradient analysis was used, in which the mixture ratio of the following solvents E and F was varied with time to temporally separate the sample solution for mass spectrometry. FIG. 3 shows the gradient profile.

Solvent E: water:ACN:formic acid 98:2:0.1
Solvent F: water:ACN:formic acid 10:90:0.1
Heating temperature: 55° C.
Temperature of sampler: 5° C.

<5.2 MS/MS Unit>

Device Name: A triple quadrupole mass spectrometer capable of MRM analysis was used (trade name: LCMS-8060, manufactured by Shimadzu Corporation). The setting values used in the relevant sections in the analysis were as follows:

CID gas pressure: 270 kPa
Interface voltage: 3 kV
Flow rate of nebulizer gas: 3 L/min.
Flow rate of heating gas: 10 L/min.
Interface temperature: 300° C.
DL temperature: 250° C.
Temperature of heat block: 400° C.
Flow rate of drying gas: 10 L/min.

FIG. 4 shows the MRM parameters for the 14 kinds of peptides. The MRM parameters include the combination of the mass-to-charge ratio of the precursor ion and that of the product ion (MRM transition), bias voltage for the Qi pre-rods, collision energy, as well as bias voltage for the Q3 pre-rods.

<5.3 Measurement Result>

Figure 5:
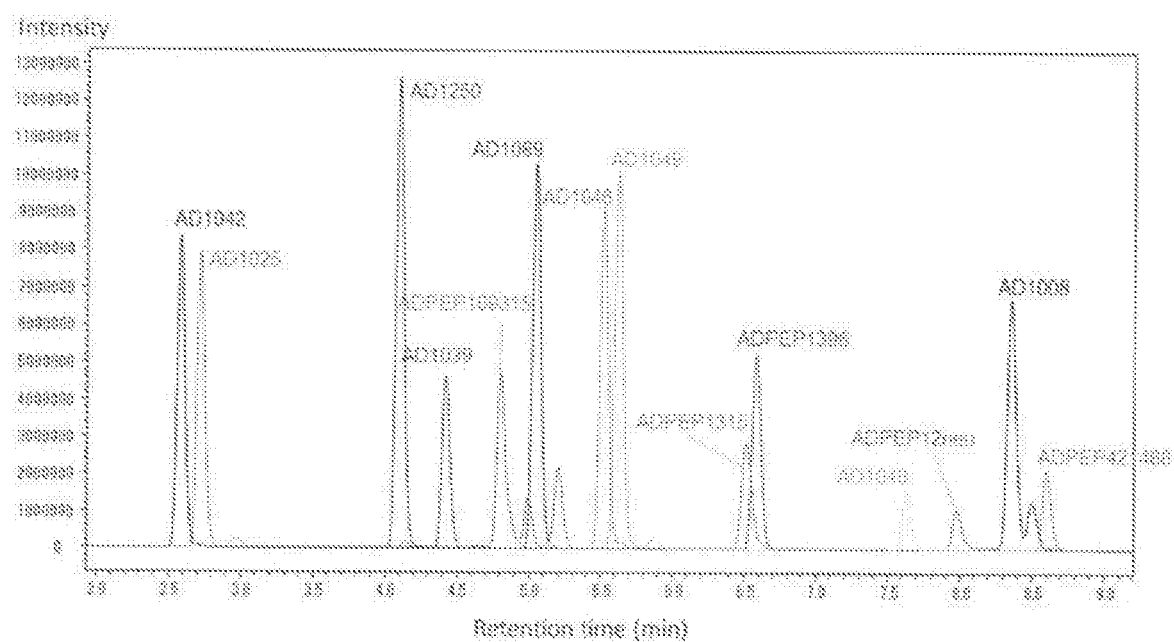
FIG. 5 is an MRM chromatogram obtained as a result of a measurement of a biological sample using a liquid chromatograph mass spectrometer according to the present embodiment.

FIG. 5 shows the base peak chromatogram created based on the ion intensifies obtained for the 14 kinds of peptides as a result of the liquid chromatograph mass spectrometric analysis performed for a biological sample collected from a subject. The codes shown in FIG. 5 correspond to those shown in Table 1. As shown in FIG. 5, the peaks originating from the 14 kinds of peptides were individually observed.

The previously described embodiment is a mere example of the present invention. For example, a gas chromatograph may be used in place of the liquid chromatograph. Solvent B (50%-100% methanol) may be used in place of solvent A (water-soluble organic solvent containing [0.1%4% TFA]+ [5%-50% ACN]) which is used in the previous embodiment to elute peptides adsorbed on the solid-phase extraction plate. In the case of using solvent B, it is preferable that the step of eluting the peptides should be followed by an additional step in which solvent B contained in the eluate is evaporated to obtain the peptides in a dried form.

The tools and devices used in the previous embodiment are mere examples and are not limited to them. For example, a C18 column, which is commonly used as the reversed phase column for liquid chromatography, may be used to construct the solid-phase extraction plate.

It is evident that any other change, modification or addition appropriately made within the spirit of the present invention will also fall within the scope of claims of the present application.

REFERENCE SIGNS LIST

10 . . . Liquid Chromatograph Unit
14 . . . Column
20 . . . MS/MS Unit
30 . . . Front Quadrupole Mass Filter
31 . . . Collision Cell
32 . . . Multipole Ion Guide
33 . . . Rear Quadrupole Mass Filter
34 . . . Ion Detector
35 . . . CID Gas Supplier
36 . . . Power Source
40 . . . Data Processing Unit
41 . . . Data Collector
42 . . . Data Storage Section
43 . . . Graph Creator
44 . . . Quantitative Analyzer
50 . . . Control Unit
52 . . . Input Unit
53 . . . Display Unit

---

The invention claimed is:

1. A disease detection method which is a method for detecting a specific disease based on a result of a measurement in which an amount of a peptide serving as a biomarker contained in a biological sample is determined by using a chromatograph mass spectrometer —including a liquid chromatograph unit and a mass spectrometer unit capable of a multiple reaction monitoring (MRM) measurement wherein:

a pretreatment process performed before the measurement using the chromatograph mass spectrometer includes steps of:

a) preparing a mixed sample solution by adding a stable isotope reagent and a trifluoroacetic acid to the biological sample, where the stable isotope reagent is prepared beforehand by labeling the peptide with a stable isotope;

b) boiling the mixed sample solution;

c) injecting the mixed sample solution after boiled into a solid-phase extraction column to make the peptide be retained in the solid-phase extraction column; and d) passing a water-soluble organic solvent through the solid-phase extraction column to elute the peptide retained in the solid-phase extraction column and collect the eluate; and a measurement using the chromatograph mass spectrometer includes steps of:

temporally separating the sample solution for mass spectrometry in the liquid chromatograph unit; and performing an MRM measurement in the mass spectrometer unit under measurement conditions including a plurality of MRM transitions corresponding to combinations of a precursor ion generated by ionization of the peptide contained in the sample solution for mass spectrometry temporally separated in the liquid chromatograph unit and a plurality of kinds of product ions formed from the precursor ion by fragmentation of amino acids at different locations in the precursor ion;

wherein the water-soluble organic solvent comprises 50%-100% methanol or the water-soluble organic solvent comprises 0.1%-1% trifluoroacetic acid and 10%-99.9% acetonitrile, and if water-soluble organic solvent is 50%-100% methanol, the method further includes following steps after the eluting step:

evaporating the water-soluble organic solvent contained in the eluate to obtain the peptide in a dried form; and preparing a sample solution for mass spectrometry by dissolving the dried peptide in an aqueous solution containing 0.1%-1% trifluoroacetic acid and 5%-50% acetonitrile;

when a concentration of the acetonitrile is within a range of 50%-99.9%, a step of preparing a sample solution for mass spectrometry by diluting the eluate so that the concentration of the acetonitrile contained in the eluate becomes lower than 50% is additionally performed after the eluting step.

2. The disease detection method according to claim 1, wherein:

the specific disease is a disease of cognitive dysfunction; and the peptide includes a peptide which is a portion of one or more proteins selected from prothrombin, gelsolin, complement C4A and complement C3.

* * * * *